United States Patent
Suhonen et al.

[11] Patent Number: 6,132,214
[45] Date of Patent: Oct. 17, 2000

[54] MEDICAL IMPLANT

[75] Inventors: Jouko Suhonen, 663 Garth Ct., Yorktown Heights, N.Y. 10598; Jens Schug, Im Mittelleimbach 11, CH-8041 Zurich, Switzerland

[73] Assignees: Jouko Suhonen, Yorktown Height, N.Y.; Jens Schug, Zurick, Switzerland

[21] Appl. No.: 09/091,674

[22] PCT Filed: Dec. 10, 1996

[86] PCT No.: PCT/EP96/05506

§ 371 Date: Aug. 12, 1998

§ 102(e) Date: Aug. 12, 1998

[87] PCT Pub. No.: WO97/22308

PCT Pub. Date: Jun. 26, 1997

[30] Foreign Application Priority Data

Dec. 18, 1995 [CH] Switzerland ............................ 3565/95

[51] Int. Cl.[7] .................................................. A61F 2/00
[52] U.S. Cl. .......................................... 433/201.1; 623/16
[58] Field of Search ............................ 433/201.1, 212.1; 623/16

[56] References Cited

U.S. PATENT DOCUMENTS

| | | | |
|---|---|---|---|
| 4,051,598 | 10/1977 | Sneer | 433/201.1 |
| 4,186,486 | 2/1980 | Gordon | 433/201.1 |
| 4,244,689 | 1/1981 | Ashman | 433/201.1 |
| 4,373,217 | 2/1983 | Draenert | 433/201.1 |
| 4,671,768 | 6/1987 | Ton . | |
| 4,842,604 | 6/1989 | Dorman et al. | 623/16 |
| 4,863,974 | 9/1989 | Mallouk et al. | 433/201.1 |
| 4,957,509 | 9/1990 | Tamari et al. | 433/201.1 |
| 5,092,890 | 3/1992 | Pohlemann et al. | 623/16 |
| 5,236,971 | 8/1993 | Murry | 433/201.1 |
| 5,356,629 | 10/1994 | Sander et al. | 623/16 |
| 5,433,751 | 7/1995 | Christel et al. | 623/16 |
| 5,476,880 | 12/1995 | Cooke et al. | 433/201.1 |
| 5,501,706 | 3/1996 | Arenberg | 433/201.1 |
| 5,520,923 | 5/1996 | Tjia et al. | 623/16 |
| 5,525,646 | 6/1996 | Lundgren et al. | 433/201.1 |
| 5,531,794 | 7/1996 | Takagi et al. | 433/201.1 |
| 5,552,454 | 9/1996 | Kretschmann et al. | 623/16 |
| 5,558,517 | 9/1996 | Shalaby et al. | 433/201.1 |
| 5,697,981 | 12/1997 | Ison et al. | 433/201.1 |

FOREIGN PATENT DOCUMENTS

| | | |
|---|---|---|
| 2658716 | 7/1977 | Germany . |
| 4432831 | 9/1995 | Germany . |

*Primary Examiner*—Todd E. Manahan
*Attorney, Agent, or Firm*—Smith Gambrell & Russell, LLP

[57] ABSTRACT

The invention relates to a medical implant, in particular a dental implant, intended for implantation in available cavities. Dental implants are implanted in extraction sockets. The implant is provided with reservoirs for a biologically active substance. An advantage of the implant is that, for dental procedures, it can be manufactured and implanted as part of a single therapeutic treatment. However, the implant can also be used as a release system for biologically active substances.

10 Claims, 16 Drawing Sheets

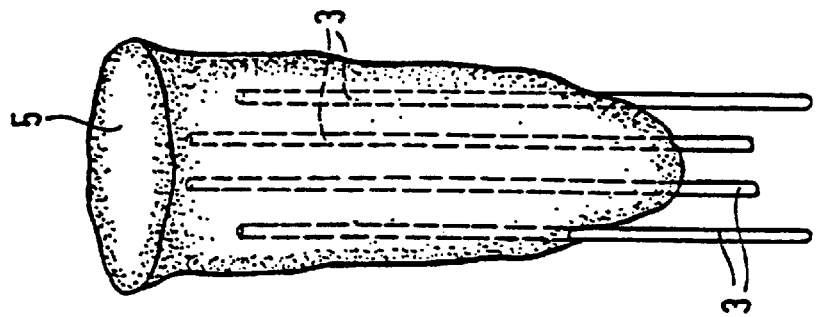
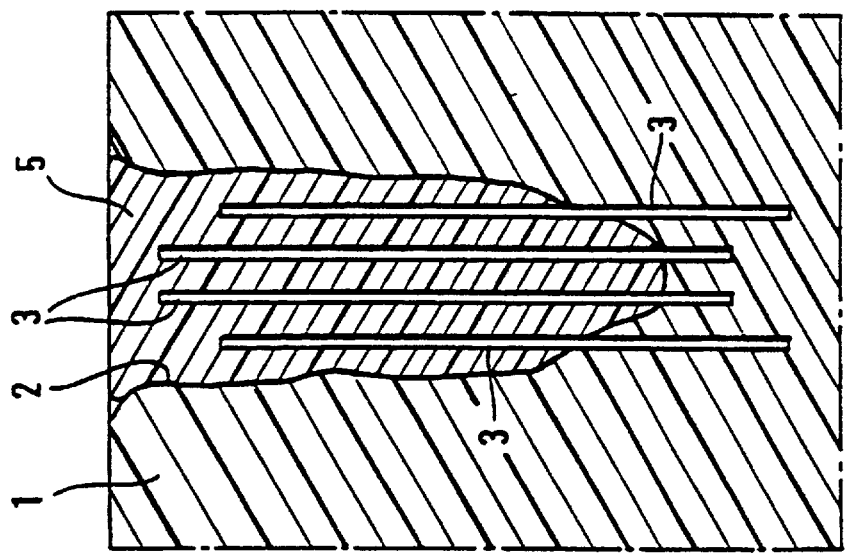
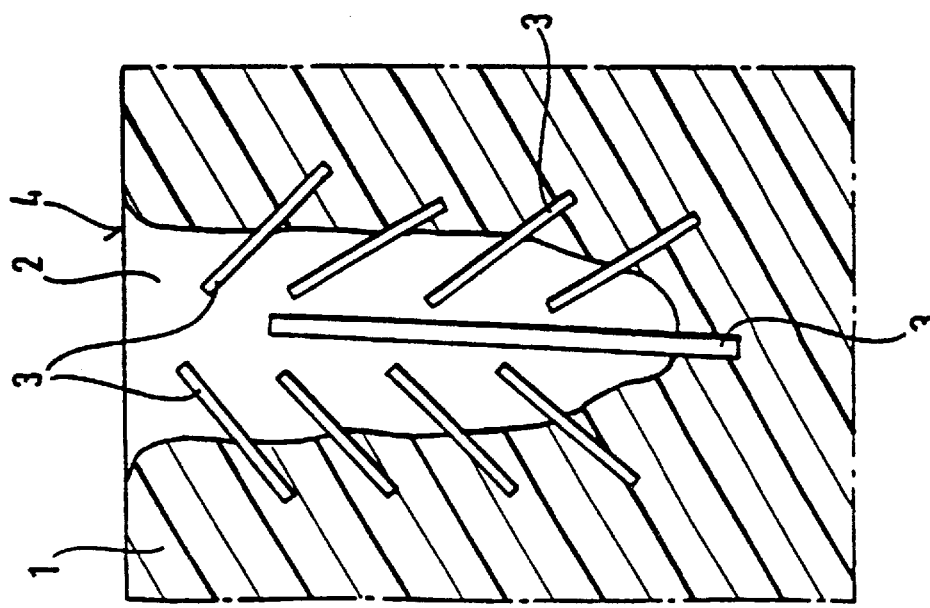

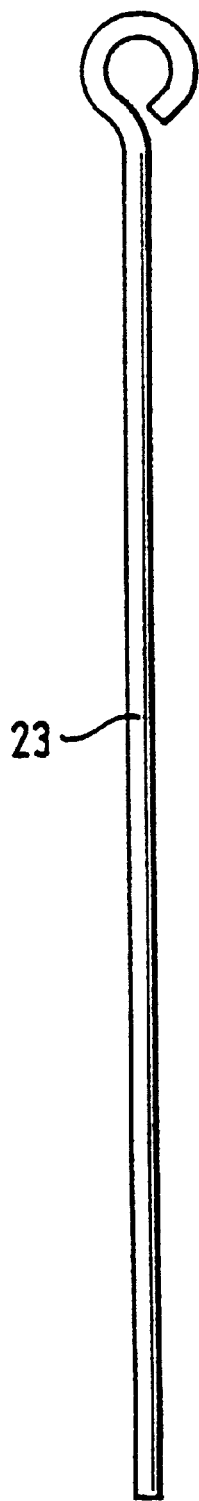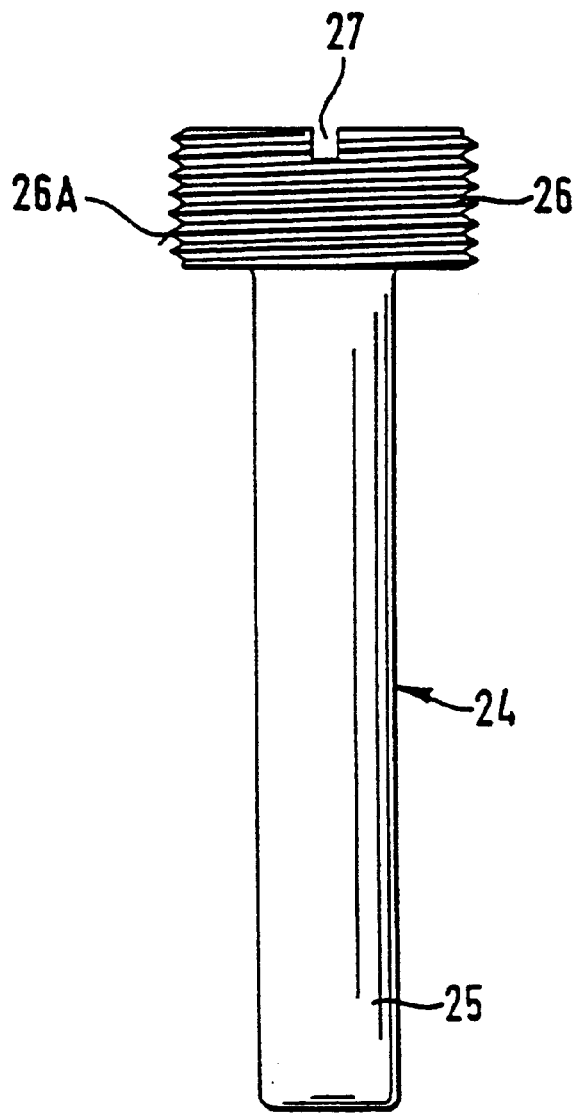
Fig. 12
Fig. 13

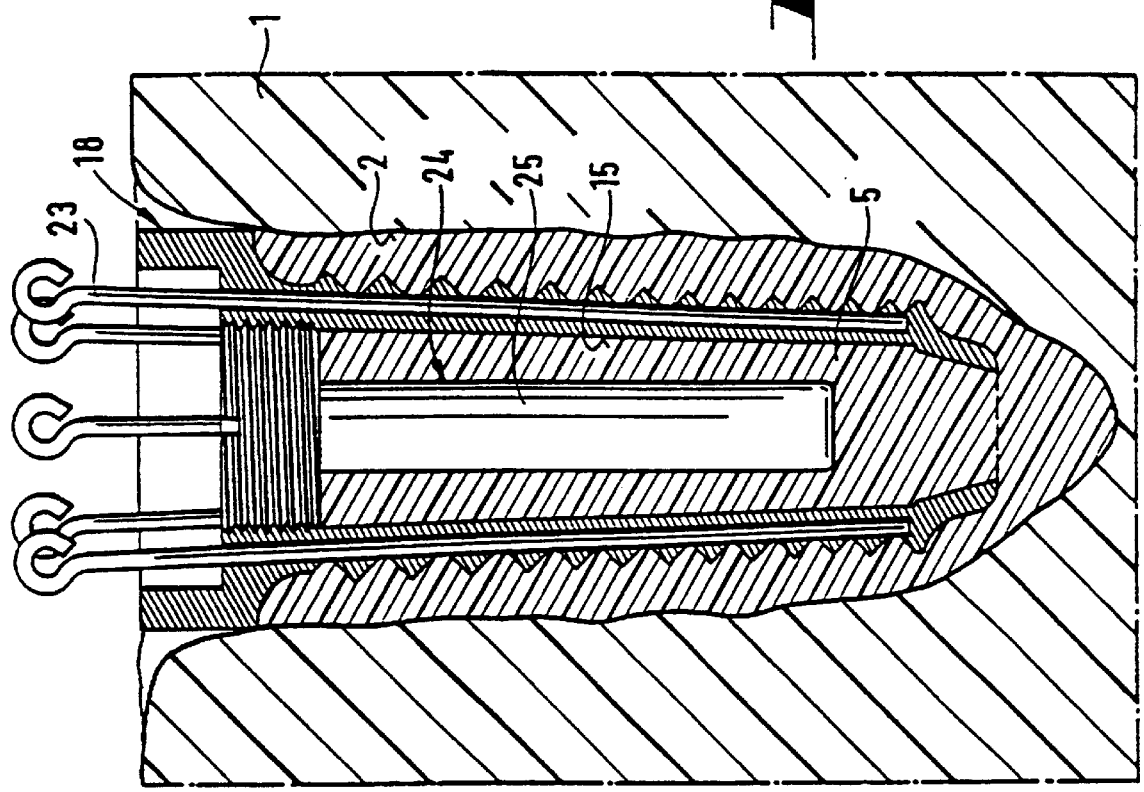
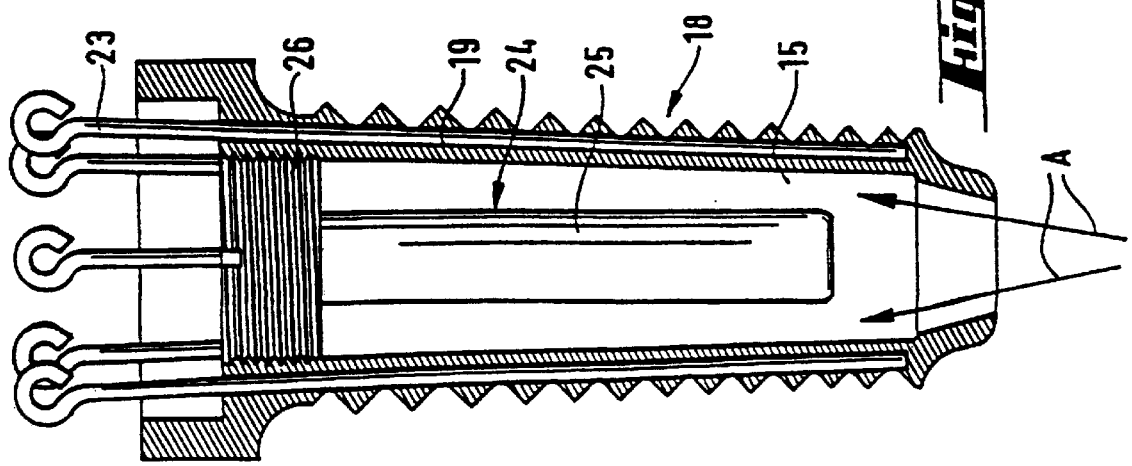

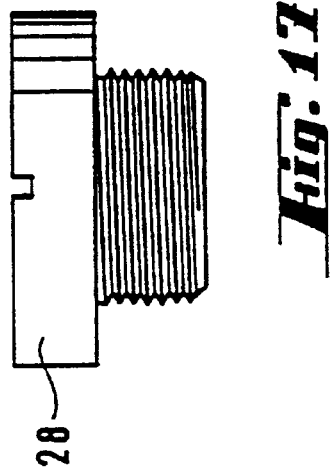
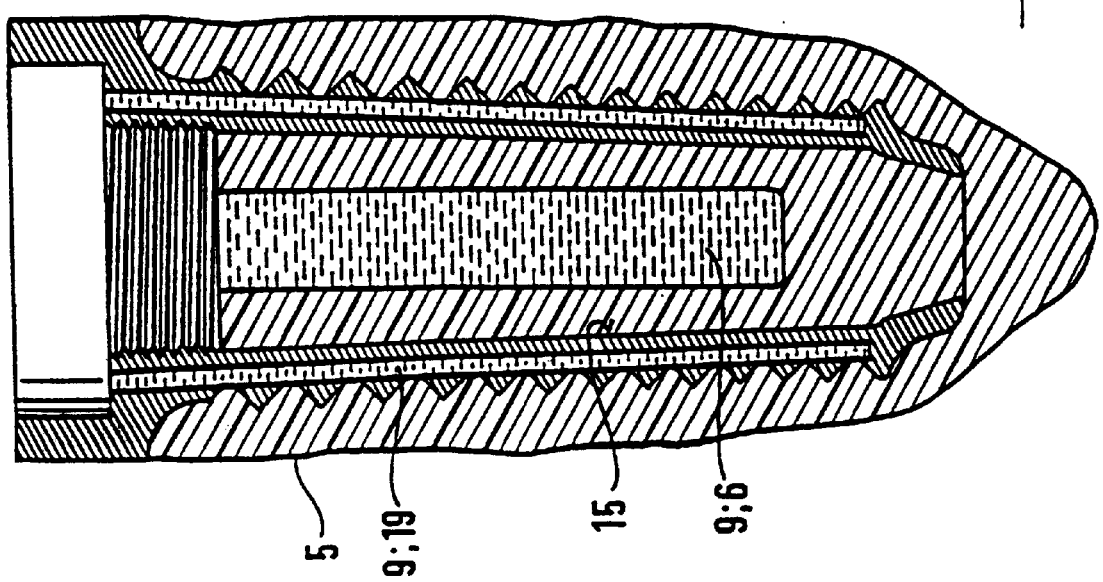

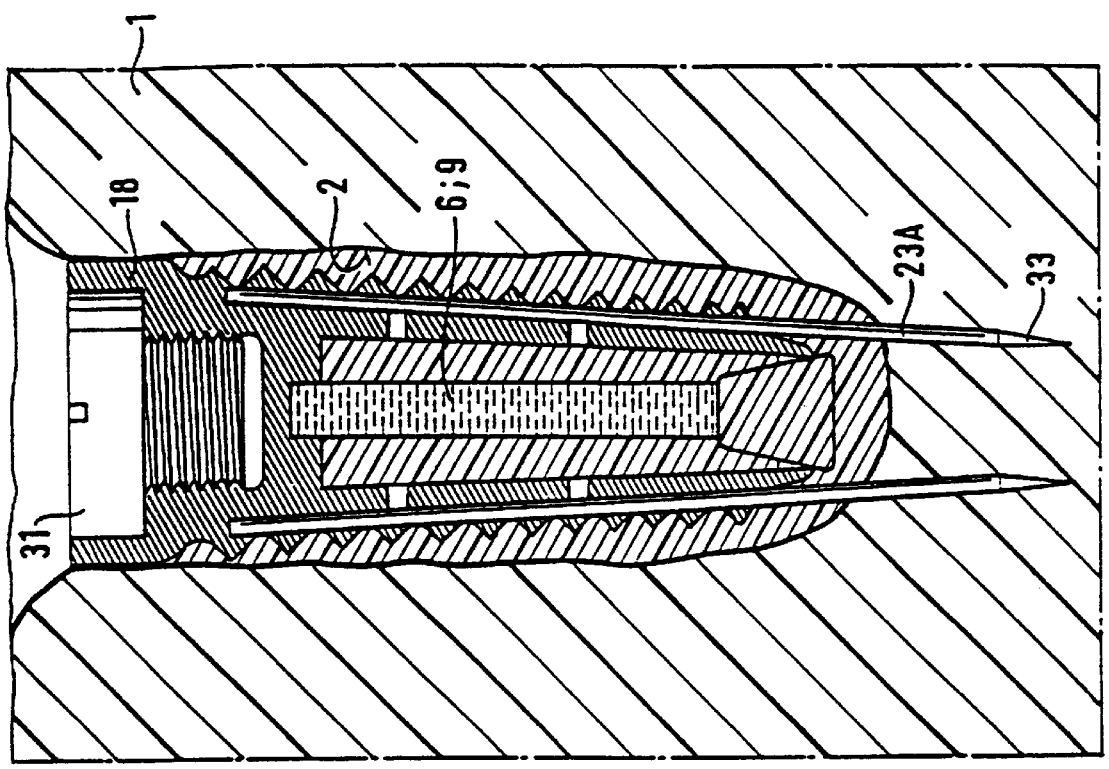
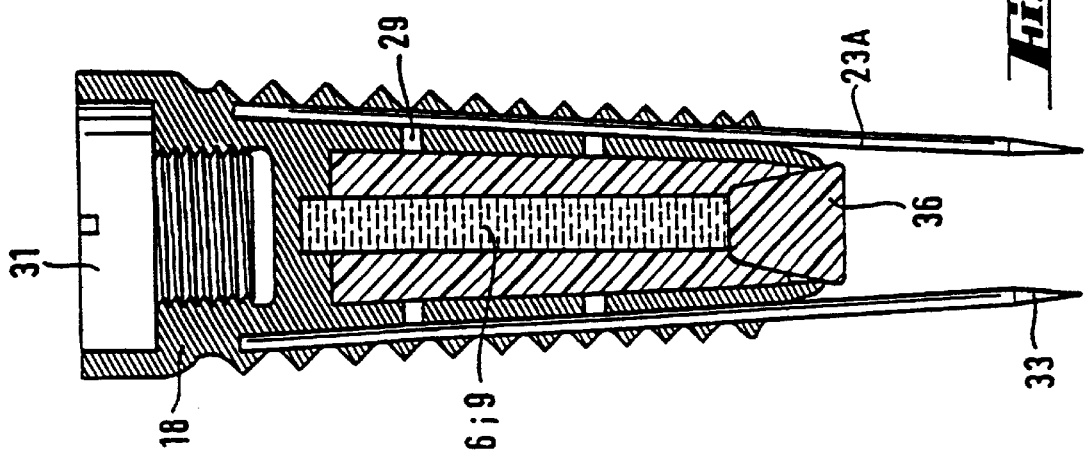

MEDICAL IMPLANT

This application was filed as international patent application PCT/EP96/05506 on Dec. 10, 1996.

INTRODUCTION AND BACKGROUND

The present invention concerns a medical implant that is intended to be inserted into a space with a prespecified dimension and to be filled and a process for producing the medical implant.

It is known that in cases of extraction wounds bones change in such a way that the space that exists due to the extraction wound can no longer be filled by an implant whose dimension and shape corresponds exactly to the extracted hard connective tissue after a certain time period.

A loss of a tooth that arises through a trauma when the tooth is unfavorably fractured and the root fragments cannot be saved can be mentioned as an example. Consequently, one must extract the fractured tooth and its root fragments. As a replacement one has been using a bridge or removable prothesis for a long time. They have the disadvantage of involving the neighboring teeth during anchoring, and if necessary, of having to be worked on. To eliminate this disadvantage one sometimes uses immediate implants instead of the lost tooth. Because up to now they have only consisted of prefabricated, standardized alloplastic materials, the extraction sockets cannot be filled by the immediate implants, which must exactly match. As a result, hollow spaces necessarily exist between the end of the socket and the implant. During the healing process these hollow spaces are filled by quickly growing connective tissue, which prevents the complete osseo-integration of the prefabricated, standardized implants. Therefore a large share of the immediate implants that have been used up to now is again lost.

As one knows, the consequence for the loss of a tooth is the atrophy of the bone in the area of the extraction socket. All bone loss in the jaw area is extremely unfavorable for the subsequent replacement of the lost tooth. Through the loss of bone volume a later implantation of a synthetic tooth root—i.e., an enossal implant—becomes difficult. Because even when the extraction wound undergoes a normal healing process some substance from the jaw bone in the area of the jaw ridge is lost, it is impossible to place the implant in the position that corresponds exactly to that of the extracted tooth and its root. Compared with the original natural position, such an implant has been strongly shifted on a horizontal and vertical level. This fact has unfavorable aesthetic and practical effects.

Implants can also be used as a replacement for other parts of the skeleton. If, for example, the lower jaw is stricken by a tumor, the area stricken by the tumor is separated from the jaw bone and replaced by an implant. In this case as well the difficulties mentioned above occur.

SUMMARY OF THE INVENTION

The present invention is based on the technical problem of shortening the time between the loss of the hard connective tissue associated with therapy—e.g., loss of bone substance, especially after the extraction of a tooth has occurred—and the insertion of an implant in such a way that bone loss of a notable dimension cannot occur.

The present invention is especially based on the technical problem of carrying out a single therapeutic treatment of the hard connective tissue as a result of a bone resection, especially with the required extraction of a tooth, and the insertion of an exactly matching individual implant in the sense of a so-called "custom-made system" at the intended site.

This problem is solved by the present invention, which concerns a medical implant for insertion into a space with a prespecified dimension—e.g., the extraction socket—and a process for producing this implant.

BRIEF DESCRIPTION OF THE DRAWINGS

FIG. 1: Cast cavity in the form of an impression of the root of a tooth, with inserted mandrels FIG. 2: Cast cavity filled with biodegradable material, with an alternative arrangement of the mandrels FIG. 3: Implant with the mandrels not yet removed

FIG. 12: Filament-shaped mandrel

FIG. 13: Mandrel with smoothbare shaft and head with screw thread

FIG. 14: Implant core according to FIG. 9 with inserted mandrel

FIG. 15: Implant core according to FIG. 14 inserted into the impression in the moulding material FIG. 16: Implant core according to FIG. 15 with filled reservoirs FIG. 17: Screw cover FIG. 21: Implant core for inserting in moulding material FIG. 22: Cast cavity filled with biodegradable material, with fixture

DETAILED DESCRIPTION OF THE INVENTION

Figure 4:
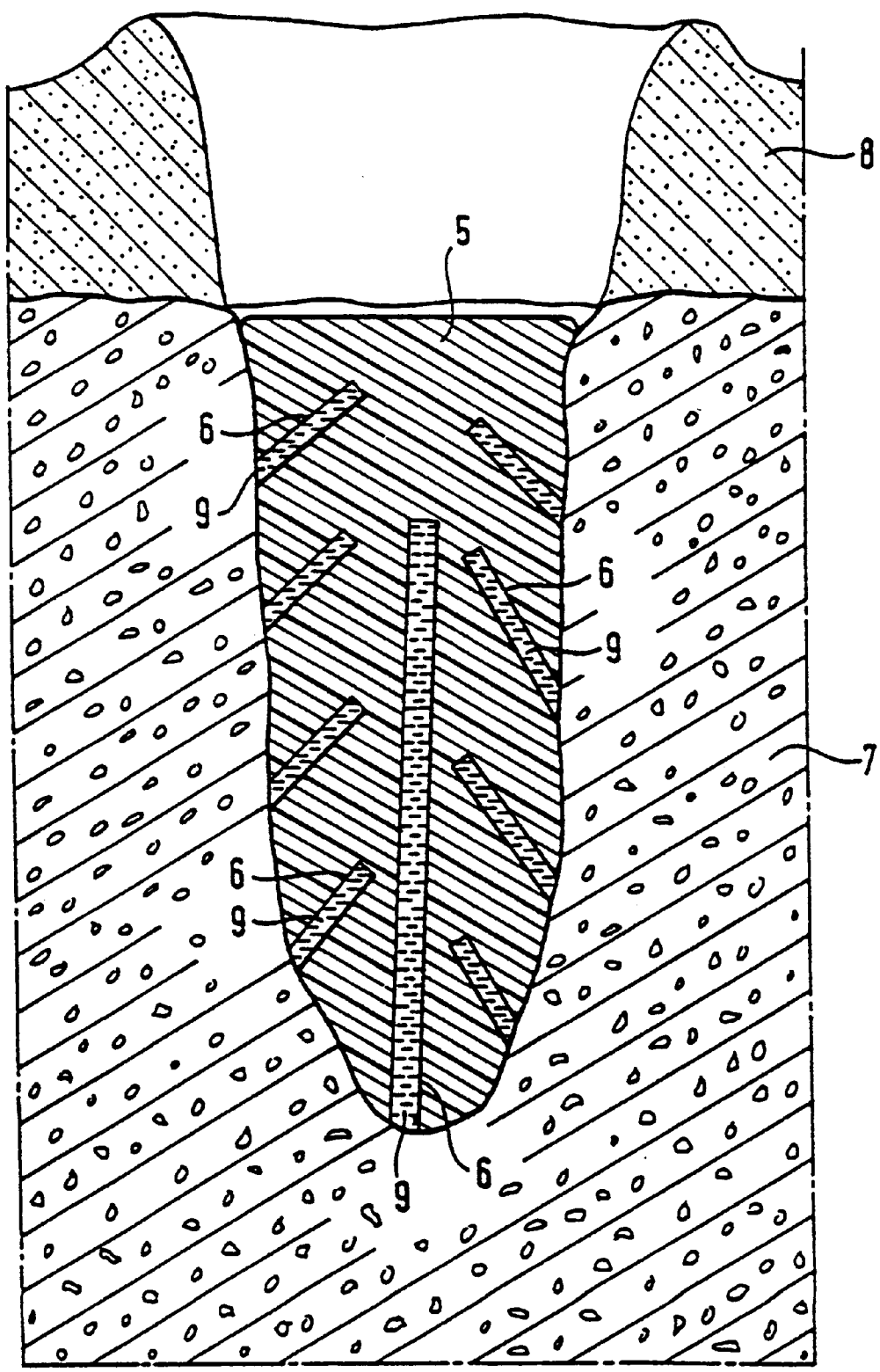
FIG. 4: Implant according to FIG. 1, which is inserted into the jaw bone and which has reservoirs with biologically active substances that arise in place of the mandrels and that are filled

The object of the invention is a medical implant 5 for insertion into a space with a prespecified dimension and for filling a cast cavity 2 with a hardening plastic material with mineral components on a basis of calcium and phosphate or, in the case of the new formation of bone, a biodegradable material, or a combination of both, characterized by the fact that a) at least one mandrel 3, or 23, 24, is placed in the cast cavity 2 in such a way that it can be removed from the cast cavity 2 of the formed implant 5 after the plastic material hardens and creates a space 6 or 19 (after its removal) that extends from the inner area of the implant 5 to its outer surface, thus forming a reservoir that can be filled with a biologically active substance, or b) the cast cavity 2 contains a porous matrix with a biologically active substance, and the hollow spaces of this matrix are filled with the hardening plastic material.

Preferably, the invention concerns tooth implants or tooth root implants. The implant has, for example, the advantage that with dental surgery, producing and implanting the individual implant can be carried out as a single therapeutic treatment. As a result, time can be saved and a traumatic second operation prevented. A second anesthesia is not necessary; nor is the added stress to the patient of another "surgery." The implantation treatment can be carried out outside of dental clinics in private practices by dentists with normal training. A high acceptance among patients can be obtained because the loss of connective tissue can be replaced immediately and with little risk. By producing and inserting the individual transplant immediately, alveolar bone loss can be prevented. Other bone fragments can also be replaced with an exactly matching, biocompatible, biodegradable fitted body, which contains a fixture made of alloplastic material in specific designs. The object of the variations of the invention is illustrated in greater detail below with the use of drawings.

The process for producing the medical implant 5 is also an object of the invention and is characterized by the fact α) that one forms a cast cavity 2 in the form of an impression of the extracted tooth or the resected bone; that one fills this cast cavity 2 with a hardening material with mineral components on the basis of calcium and phosphate or, in the case of the new formation of bone, a biodegradable material; that one places at least one mandrel 3, or 23, 24, in the cast cavity 2 in such a way that it can be removed from the cast cavity 2 of the formed implant after the plastic material hardens and with the removal of the mandrel a space 6, or 19, forms that serves as a reservoir and extends from the inner area of the implant 5 to its outer surface; and that one fills the reservoir with a biologically active substance after removing the mandrel 3, or 23, 24, or β) that one forms a cast cavity 2 in the form of an impression of the extracted tooth or the resected bone; that one fills the cast cavity 2 with a porous matrix that contains a biologically active substance and the hollow spaces of this matrix with the hardening plastic material.

Also an object of the invention is a nontherapeutic process for producing the medical implant 5, which is carried out outside of a human or animal's body and is characterized by the fact α') that one forms a cast cavity 2 in moulding material 1 in the form of an impression of the extracted tooth or the resected bone; that one fills this cast cavity 2 with a hardening material with mineral components on the basis of calcium and phosphate or, in the case of the new formation of bone, a biodegradable material; that one places at least one mandrel 3, or 23, 24, in the cast cavity 2 in such a way that it can be removed from the cast cavity 2 of the formed implant after the plastic material hardens and with the removal of the mandrel forms a space 6, or 19, serving as a reservoir, that extends from the inner area of the implant 5 to the outer surface; that one removes the formed implant 5 from the cast cavity and fills the reservoir with a biologically active substance after the removal of the mandrel 3, or 23, 24, or β') that one forms a cast cavity 2 in moulding material 1 in the form of an impression of the extracted tooth or the resected bone; that one fills the cast cavity 2 with a porous matrix that contains a biologically active substance and the hollow spaces of this matrix with the hardening plastic material and removes the formed implant 5 of the cast cavity.

An especially preferred variation of the procedure is characterized by the fact that one first places in the cast cavity 2 several mandrels 3, or 23, 24, that extend from the cast cavity 2 into the moulding material 1 and are placed in the moulding material 1 in such a way that one can remove the mandrels 3, or 23, 24, from the implant after pouring the plastic moulding material into the cast cavity 2, letting it harden, and then removing the formed implant 5 from the cast cavity 2.

The invention will be further understood by the following Examples:

EXAMPLE 1

In FIGS. 1–4 a first working Example of the invention and its production process is illustrated, whereby the implant fills a bone defect that has arisen from the extraction of a tooth.

FIG. 1: At first the involved tooth is extracted. If there is a fracture, its fragments—especially the root—are agglutinated. The contaminated root surface of the tooth is cleaned aseptically, mechanically, and/or chemically. The tooth is then pressed into moulding material 1 up to the tooth neck by a known method; the moulding material is a sterile, elastic moulding compound of a known type such as alginates, silicone cross-linked with additives and condensation, polyether, etc. After the moulding material 1 hardens, the tooth is taken out, and a cast cavity 2 in the form of an impression of the dental implant to be produced is formed in the moulding material 1.

Several mandrels 3 in the form of filaments or rods made of smooth material that resists breakage are inserted from the cast cavity into this moulding material. The term mandrel includes objects and devices that are used as place holders for reservoirs or hollow spaces that can be filled. The filament- or rod-shaped mandrels 3 are placed in such a way that they do not reach the level 4 of the limbus alveolaris. As a result, a cast cavity 2 in which the mandrels 3 are arranged as shown in FIG. 3 is formed in the moulding material 1.

This cast cavity 2 is then filled with a hardening plastic material with mineral components on the basis of calcium and phosphate or, in the case of the new formation of bone, a biodegradable material, or a combination of the two.

Plastic materials with mineral components on the basis of calcium and phosphate (CPHC: calcium phosphate hydraulic cements) can be obtained by combining partly neutralized phosphate materials and calcium salts in accordance with the procedure described in European patent application 416 761. Suitable phosphate materials are, for example, $Ca(H_2PO_4)_2 \cdot H_2O$ [MCPM], $CaHPO_4 \cdot H_2O$ [DCPD:

brushite], $Ca_9(HPO_4)\cdot(PO_4)_5(OH)$ [CDHA: calcium-deficient hydroxyapatite], $Ca_3(PO_4)_2$ [α- or β-tricalcium phosphate: TCP], $Ca_5(PO_4)_3(OH)$ [OHAP: hydroxyapatite], $Ca_{28}(PO_4)_{15}(CO_3)_3(OH)_5$ [CHAP: carbonated hydroxyapatite], $Ca_2P_2O_7$ [CPP: calcium pyrophosphate], $CaSO_4\cdot0.5H_2O$ [CHS: "Plaster of Paris"], $CaSO_4\cdot2H_2O$ [CSD: plaster], $CaCO_3$ [CC: calcite], or mixtures thereof.

Preferred is a plastic material with mineral components on the basis of calcium and phosphate with the following shares: 60–80% β-TCP, 40–20% MCPM, an aqueous solution containing $P_2O_7^{4-}$ and $SO_4^{2-}$ ions and additives of the cellulose ether type, for example, HPMC (0.5–1.0%) or polysaccharides.

Materials suitable for the new formation of bone have osteo-conductive properties and are preferably biodegradable and biocompatible. Osteo-conductive materials control the make-up of a structure for the new formation of bone during "guided bone repair" (GBR).

Biodegradable and biocompatible materials are generally known—e.g., aliphatic polyesters of the types polyglycolic acid (PGA) or polylactic acid (PLA) and their compounds (PGA/PLA); enantiomeric forms and racemic compounds in various proportions, e.g., poly-L-lactate (PLLA), poly-D-lactate (PDLA), poly-DL-lactate (PDLLA), L-lactate/DL-lactate, or L-lactate/D-lactate. These materials are not only biodegradable, they are also biocompatible. PGA and PLA have metabolism channels (pathways) in the human body. Furthermore, PGA and PLA materials are not immunogens—that is, these materials do not cause immune reactions in mammals. Suitable materials are, for example, commercial products of the type Biofix®, which can be obtained commercially from the firm Bioscience (SF-33721 Tampere).

Suitable aliphatic polyesters with osteo-conductive properties are, in addition, PLA copolymers, e.g., lactate/tetramethyleneglycolid copolymers, lactate/trimethylene carbonate copolymers, lactate/α-valerolactone copolymers, lactate/ε-caprolactam copolymeres, polydepsipeptide (glycine-DL-lactate copolymers or PLA/ethylene oxide copolymers (PLA/PEO)), polylactide-polyglycolid copolymers or polylactide-ethylene oxide copolymers or polyhydroxyalkanoates, e.g., PHB [Poly(β-hydroxybutyrate)], PHB/PHA (polyhydroxybutyrate/polyhydroxyvalerate), PCL [poly(ε-caprolactam), PDS [poly(p-dioxanone)], polyanhydrides, polyhydroxysuccinic acid (β) or polyhydroxysuccinic acid ester.

Suitable materials for the new formation of bones that have osteo-conductive properties are, in addition, vinyl polymers, e.g., on the basis of polyvinyl alcohol (PVA), poly-β-maleic acid, aliphatic polyamides, aliphatic polyurethanes, e.g., polyurethanes made of polyethyleneglycol-(PEG)-diols or polycaprolactam-diols and diisocyanates such as 1,4-methylene diisocyanate, polyorthoesters, e.g., of the type Alzmer® (Alza Corp.) or DETOSU, aliphatic polyanhydrides, polypeptides, e.g., synthetic polyamino acids and poly-α-amino acids, e.g., poly-β-lysine or polybenzylglutamate, polyphosphates, polysaccharides, e.g. dextran derivatives, chitin derivatives, and chitosan derivatives or hyaluronic acid esters, modified proteins, e.g., cross-linked collagen or fibrin, or modified carbohydrate polymers.

Also suitable are their composites and the block and graft copolymers of the polymers and copolymers mentioned.

The plastic materials named can be put into place in the cast cavity 2 by using suitable filling instruments, e.g., injection instruments.

FIG. 2: FIG. 2 shows a cast cavity, filled with biodegradable material, that has taken the form of the implant 5 after the plastic material has hardened. Compared with the model in FIG. 1, the mandrels 3 here have an alternative arrangement and design.

FIG. 3: After the materials for implant 5 have hardened it is removed from the cast cavity 2 together with the mandrels 3. Then the filament-shaped mandrels 3 are pulled out of the implant 5. In this way, channel- and capillary-shaped spaces or gaps 6 are formed in the implant 5, which serve as reservoirs for biologically active substances (so-called active substances).

Suitable biologically active substances are poured into the reservoirs. They have osteo-conductive properties and can have an effect on the biological behavior of neighboring cells, for example, by stimulating the division of cells or the formation of bone, through, e.g., the formation of mesenchymal cells, endothelial tissue, pericytes, osteoclasts, osteoblasts, etc. Suitable biologically active substances with osteo-conductive properties are, for example, hormones, proteins or growth factors on a protein or lipid basis that are known by such names as epidermal growth factor (EGF); vascular epidermal growth factor (VEGF); fibroblast growth factor (FGF); platelet derived growth factor (PDGF); transforming growth factor-β(TGF-β), e.g., of the type TGF-β-1, TGF-β-2, or TGF-β-3; insulin-like growth factor (IGF-I and IGF-II); nerve growth factor (NGF); bone morphogenic proteins (BMP), e.g., BMP-3 (osteogenin), BMP-2 (BMP 2A), BMP-4 (BMP 2B), BMP-5, BMP-6, BMP-7 (osteogenic protein-1); and proteins that are known by the names parathyroid hormone (PTH), e.g., PTH fragments such as FTH 1–34 and its derivatives; parathyroid hormone related proteins (PTHrP), e.g., PTHrP fragments, e.g., PTHrP 1–34 and its derivative osteoglycin, cartilage induction factor and skeletal growth factor. Bone growth factors on a lipid basis include prostanoids, which are known by the names prostaglandins A, D, E, F, I and derivatives of them such as prostacyclin.

Proteins (active components) with the properties of a transformed growth factor of type beta (TGF-β) are known and described in the survey article from A. B. Roberts and M. B. Sporn, "The Transforming Growth Factor-βs," in the *Handbook of Experimental Pharmacology: Peptide Growth Factors and Their Receptors,* edited by M. B. Sporn and A. B. Roberts. New York: Springer Verlag, pp. 419–72.

Proteins of the type TGF-β of human origin are known and described in the survey article by D. A. Cox, "Transforming Growth Factor-Beta 3." *Cell Biology International* 19, no. 5 (1995): 357–71.

Recombinant proteins of type TGF-β are known and described in the following survey article: Lionel Bourdel, et al. "Recombinant Human Transforming Growth Factor-β1: Expression by Chinese Hamster Ovary Cells, Isolation and Characterization." *Protein Expression and Purification* 4 (1993): 130–40; M. P. Schlunegger and M. G. Grütter. "An Unusual Feature Revealed by the Crystal Structure at a Resolution of Human Transforming Growth Factor-β 2." *Nature* 358 (1992): 430–34; S. Runser and N. Cerietti. "Transforming Growth Factors β: Conformational Stability and Features of the Denaturation of Recombinant Human Transforming Growth Factors-β 2 and β 3." *Biotechnol. Appl. Biochem.* 22 (1995): 39–53.

Proteins with the properties of a transforming growth factor of type beta (TGF-β) chosen from the group consisting of TGF-β 1, TGF-β 2, TGF-β 3, and TGF-β 5 and bone-morphogenic proteins (BMP) are known and described in the survey article by D. M. Kingsley, "The TGF-β Superfamily: New Members, New Receptors, and New Genetic Tests of Function in Different Organisms." *Genes and Development* 8 (1994): 133–46.

Additional substances that can be poured into the reservoirs mentioned are active substances that inhibit bone resorption, e.g., bisphosphonates of the type Aredia®, nitrates, e.g., nitroglycerin, ipriflavon, active substances that bind with nuclear receptors such as estradiol, enzyme inhibitors that block enzymes that break down the bone matrix, collagenase inhibitors, stromelysine [Stromelysin] inhibitors, cathepsin L, K inhibitors, substances that inhibit osteoclast functions such as carboanhydrase inhibitors or inhibitors of the osteoclastic proton pump, etc.

Other active substances are those that are effective against inplantopathogens (paradontophathogens), e.g., antibiotics, antibodies (monoclonal, polyclonal), inflammation inhibitors, prostaglandin inhibitors, active substances with immune-suppressive effects such as (bio)synthetic immune suppressors, active substances with revascularization-promoting effects such as vascular-forming substances, active substances that promote circulation, or analgesics. Before inserting the implant, one pours the biologically active substances that are to be dispensed, or combinations of such substances, into the reservoir 6. The biologically active substances mentioned, for example, can be poured into the reservoirs by using traditional medical injection instruments.

The implant filled with the biologically active substance represents a "dispensing unit," which contains a dose of the substance to be dispensed and releases it within a set time period. A dispensing unit as defined here contains one dose of the substance to be dispensed, or a faction or multiple of it. It can be dispensed spontaneously, e.g., by diffusion or erosion of the system through interaction with body fluids.

FIG. 4: One places the exactly matching implant 5 in the socket in the jaw bone 7, whereby in FIG. 4 the gingiva 8 is also implied. In so doing the substances 9 are released from the implanted implant.

EXAMPLE 2

Another working example of the invention that is especially well suited for use as a dispensing unit is represented in FIGS. 5–9.

Figure 5:
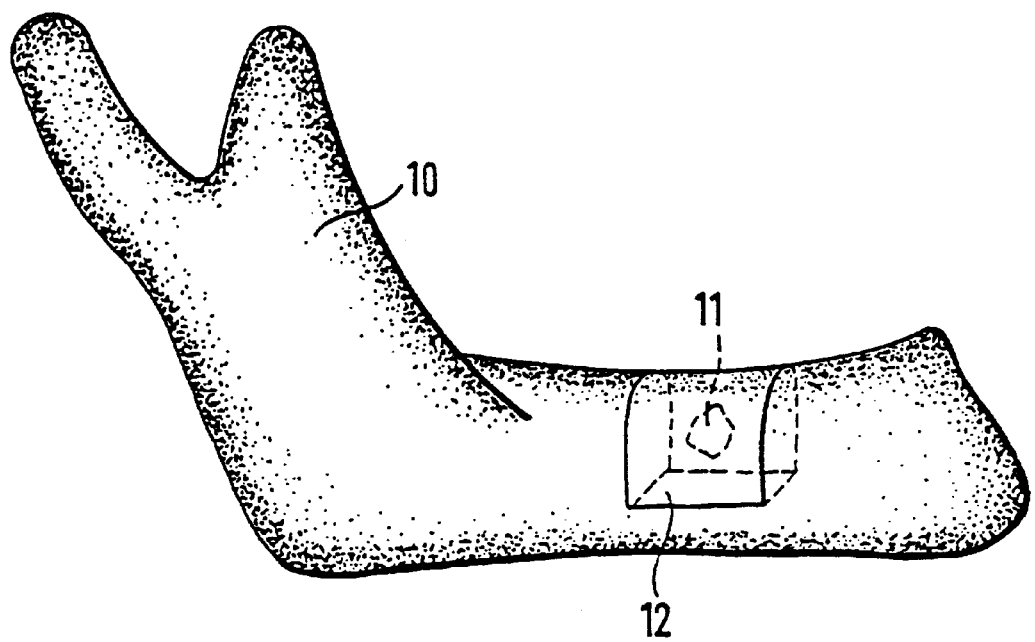
FIG. 5: Part of the lower jaw to illustrate another working example of the invention
Figure 6:
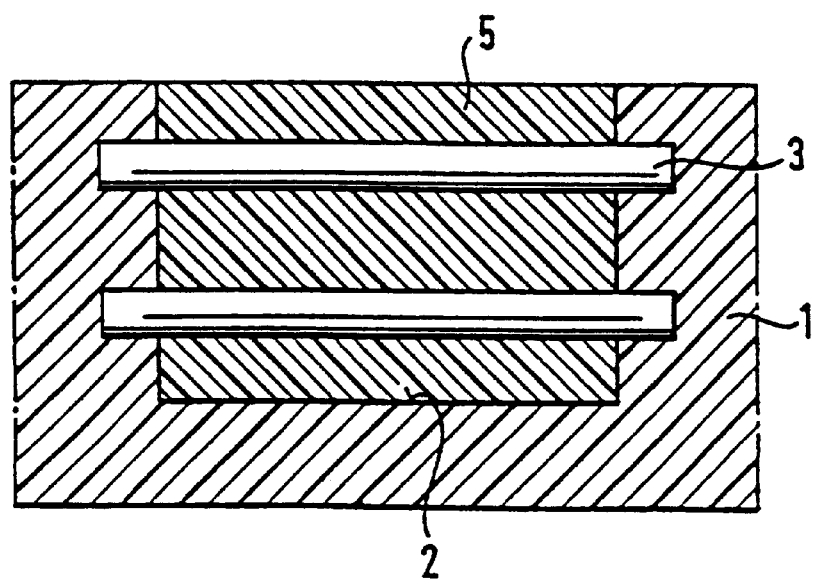
FIG. 6: Moulding material that contains the mandrels for forming reservoirs and that is filled with a biodegradable material to form one of the implants corresponding to the resection defect

FIG. 5: FIG. 5 shows a lower jaw 10 in which a tumor 11 has formed. The bone part 12 stricken with the tumor 11 is removed from the lower jaw 10 and then an impression is made in the moulding material 1 (see the section according to FIG. 6). The mandrels 3 are placed in the cast cavity 2 so their ends project out of the moulding material 1. The arrangement of the mandrels 3 shown in FIG. 6 is reproduced as an example and can vary. After inserting the mandrels 3, the cast cavity 2 is filled with the biodegradable material that hardens into an implant 5.

FIG. 6: The bone part 12 removed from the lower jaw 10 according to the drawing in FIG. 6 is pressed into the moulding material 1 and rotated by 180° compared to the drawing in FIG. 5 so that the upper, rounded section of the bone part 12, in accordance with the drawing in FIG. 6, is located at the bottom as shown in FIG. 6. The remaining spaces or reservoirs 6 in the implant 5 after removing the mandrels 3, as described above, are filled with one or several active substances 9.

Figure 7:
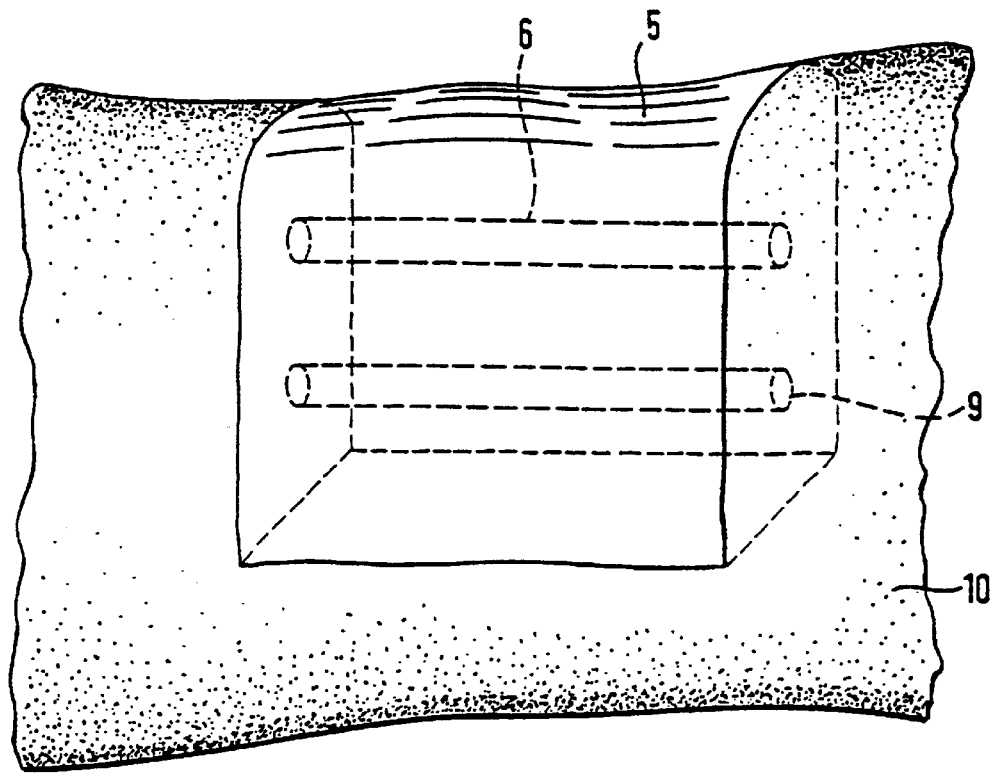
FIG. 7: Implanted implant with filled reservoirs

FIG. 7: The implant 5 is implanted into the intended site in the lower jaw 10, as is shown in FIG. 7.

Figure 8:
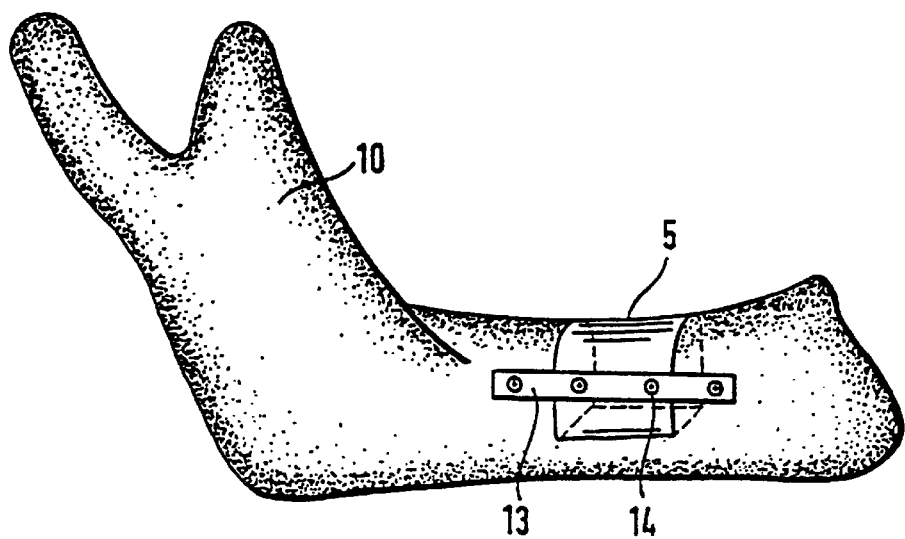
FIG. 8: Lower jaw with implant affixed to it

FIG. 8: If necessary, one can attach the implant 5 by using a plate 13 in the jaw bone, whereby the plate 13 as well as the screws 14 belonging to it can also consist of a biodegradable material.

EXAMPLE 3

With the use of FIGS. 9–18 another working example of the invention is described.

Figure 9:
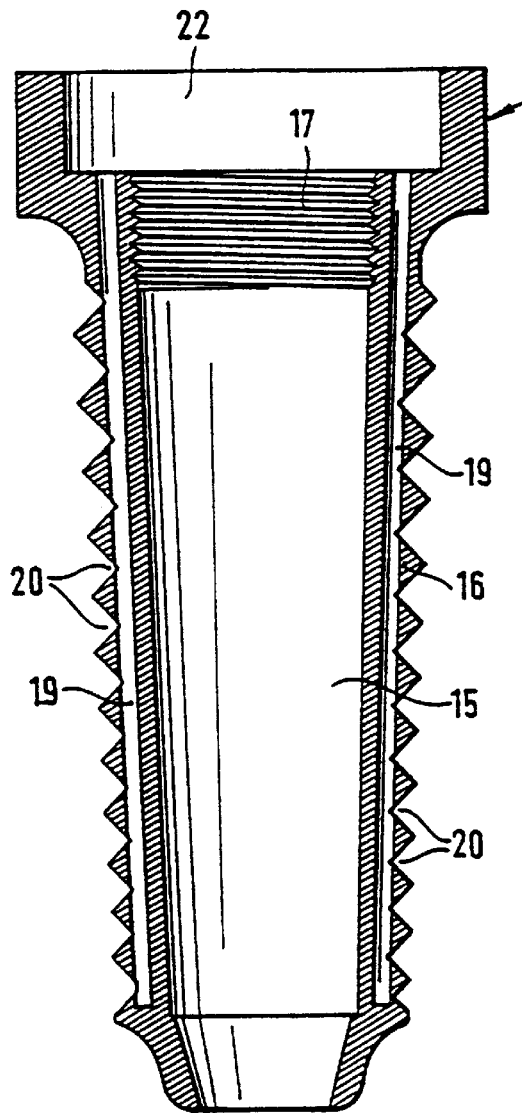
FIG. 9: Cut through an implant core serving as a fixture according to another working example of the invention

FIG. 9: FIG. 9 shows a sectional view of an implant core that also serves as a fixture. The term fixture designates the enossal part (inside the jaw bone) of an implant, which takes up the part of an implant construction (the visible part of the implant) projecting from the jaw bone. Such an implant core consists of an alloplastic, osseo-integratable material, e.g., titanium, Frialit, etc. It has the form of an elongated hollow body 18 with an inner space 15. Its outer side is structured, for example, in the form of a screw thread 16. Other designs also provide for a structuring of the inner side. An inside screw thread 17 is designed at the upper end of the inner space 15. In the wall of the hollow body 18 hollow spaces 19 that run parallel to the inner space 15 exist and are open at the top and closed at the bottom—i.e., at the end far away from the inside screw thread 17. Another arrangement of the hollow spaces 19 is possible as an alternative to the parallel arrangement to the inner space 15. As is clear from FIG. 9, the hollow body 18 is tapered to the lower end, i.e., to the root tip. The inside screw thread 17 at the upper wider end, i.e., in the area of the limbus alveolaris, not only serves to seal the reservoir of active substances, as will be described later, but also to attach the suprastructure later when the tooth is restored or to attach the prosthesis with help of the implant. The hollow spaces 19 in the wall of the hollow body 18 are arranged in such a way that they cut the grooves of the screw thread 16 or the respective structure of the wall of the hollow body 18. Moreover, perforations 20 exist in the wall that run from the hollow spaces 19 to the outer surface of the hollow body.

Figure 9A:
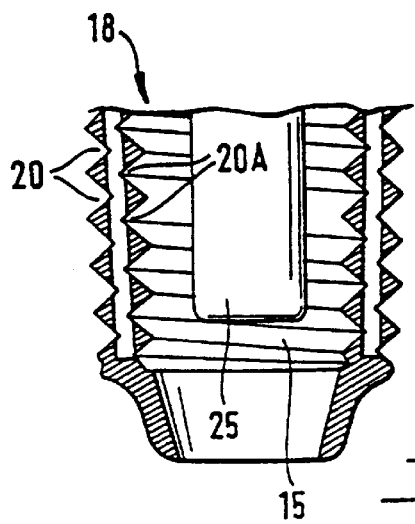
FIG. 9A: Section of FIG. 9 with a variation of a structured inner side of the implant core according to FIG. 9.

FIG. 9A: An alternative arrangement of the perforations is shown in FIG. 9A, which represents a cut from FIG. 9. In this design the inner surface of the hollow body 18 is also structured. In this connection additional perforations 20A, which run from the hollow spaces 19 to the inner surface of the hollow body 18, exist and connect the hollow spaces 19 with the inner space 15 of the hollow body 18. A design is also provided in which only the inner surface of the hollow body 18 is structured.

Figure 10:
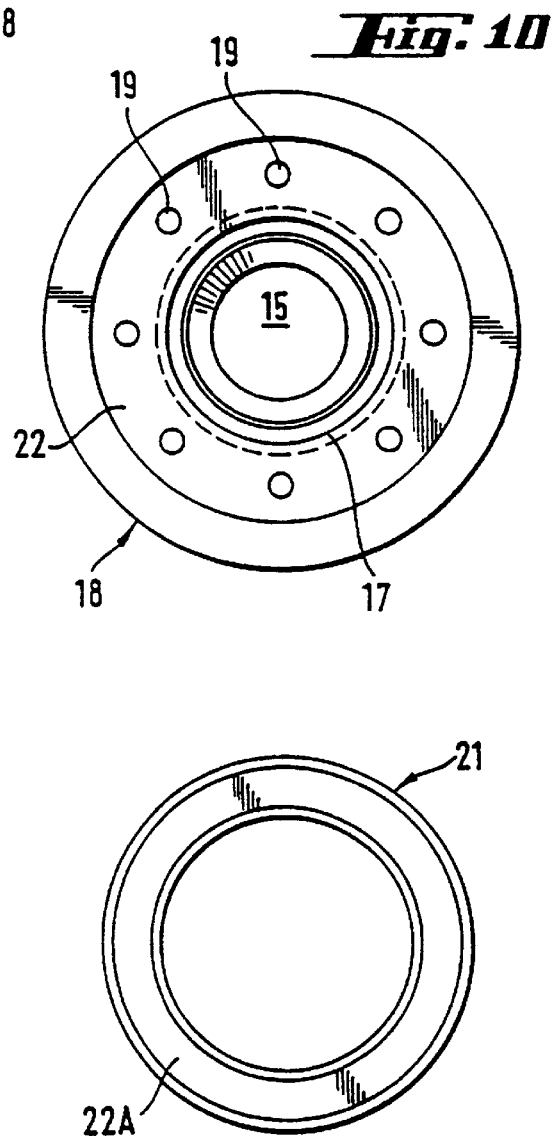
FIG. 10: View onto the implant core according to FIG. 9

FIG. 10: FIG. 10 represents the view onto the implant core in accordance with FIG. 9.

Figure 11:
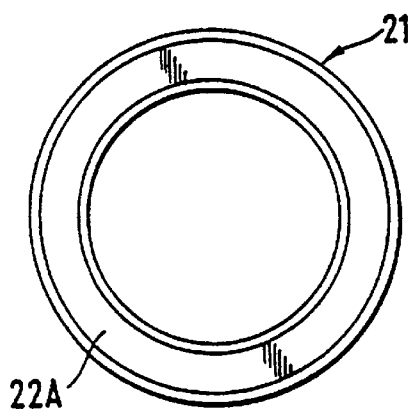
FIG. 11: Washer

FIG. 11: FIG. 11 shows a packing ring 21 that is intended for insertion into the upper, recessed end section 22 of the hollow body 18. This packing ring 21 can consist of silicone rubber or soft gold or plastic sealing metal beads so that, with the packing ring 21 inserted into the area 22 A, the openings to the hollow spaces 19 and the hollow space 15 are safely closed off to outside influences, e.g., the penetration of pathogens (bacteria, yeasts, viruses, etc.).

FIG. 12: FIG. 12 shows a filament-shaped mandrel 23. Its diameter is calculated in such a way that it can be inserted into a respective hollow space 19.

FIG. 13: In FIG. 13 another mandrel 24 is designed that consists of a shaft 25 and a head 26 that has an exterior screw thread 26 A and a slit 27 at the top for accommodating a screwdriver like tool.

FIG. 14: To produce an implant, first the mandrel 24, which has a shaft 25 and head 26, is screwed into the inner space 15 of the hollow body 18. Then the filament-shaped mandrels 23 are inserted into the respective hollow spaces 19. In a first step, a first amount of a plastic biodegradable material is placed in the inner space 15 from below in the direction of arrow A.

FIG. 15: An impression of the root of the tooth to be replaced by the implant—that is, the cast cavity 2—is produced in the moulding material 1. In a second step, a second amount of the biodegradable material is poured into the cast cavity; and in a third step the hollow body 18, already filled and equipped with the mandrels 23 and 24, is pressed into the still liquid biodegradable material. To pour it the biodegradable material is liquified by warming it (in special application syringes or another way) depending on its composition, or it is available in liquid or plastic form at room temperature. Thickening and hardening ensues either by cooling the thermoplastic material or through a chemical reaction (e.g., a 2-component reaction, a photochemical process, or polymerization, etc.). It is clear from FIG. 15 how the gap between the outer wall of the hollow body 18 and the inner wall of the cast cavity 2 in the moulding material 1 is filled by this material. After the material hardens, the implant 5, in which the hollow body 18 that still has the mandrels 23 and 24 is imbedded, exists. The implant 5 is removed from the moulding material 1 and then the filament-shaped mandrels 23 and the mandrel 24 are pulled and screwed out, respectively, of the implant 5.

FIG. 16, FIG. 17: The biologically active substances described earlier can be poured into the remaining spaces 6. The spaces 6 are closed off at the top by the screw cover 28 (FIG. 17). In this way an implant 5 is formed that has an alloplastic fixture (hollow body 18) on the inside, which is surrounded by a biodegradable material. Reservoirs 19, 15 for active substances exist. The implant, anatomically replicated to correspond to the extracted root, is ready to be placed in the extraction socket.

Figure 18:
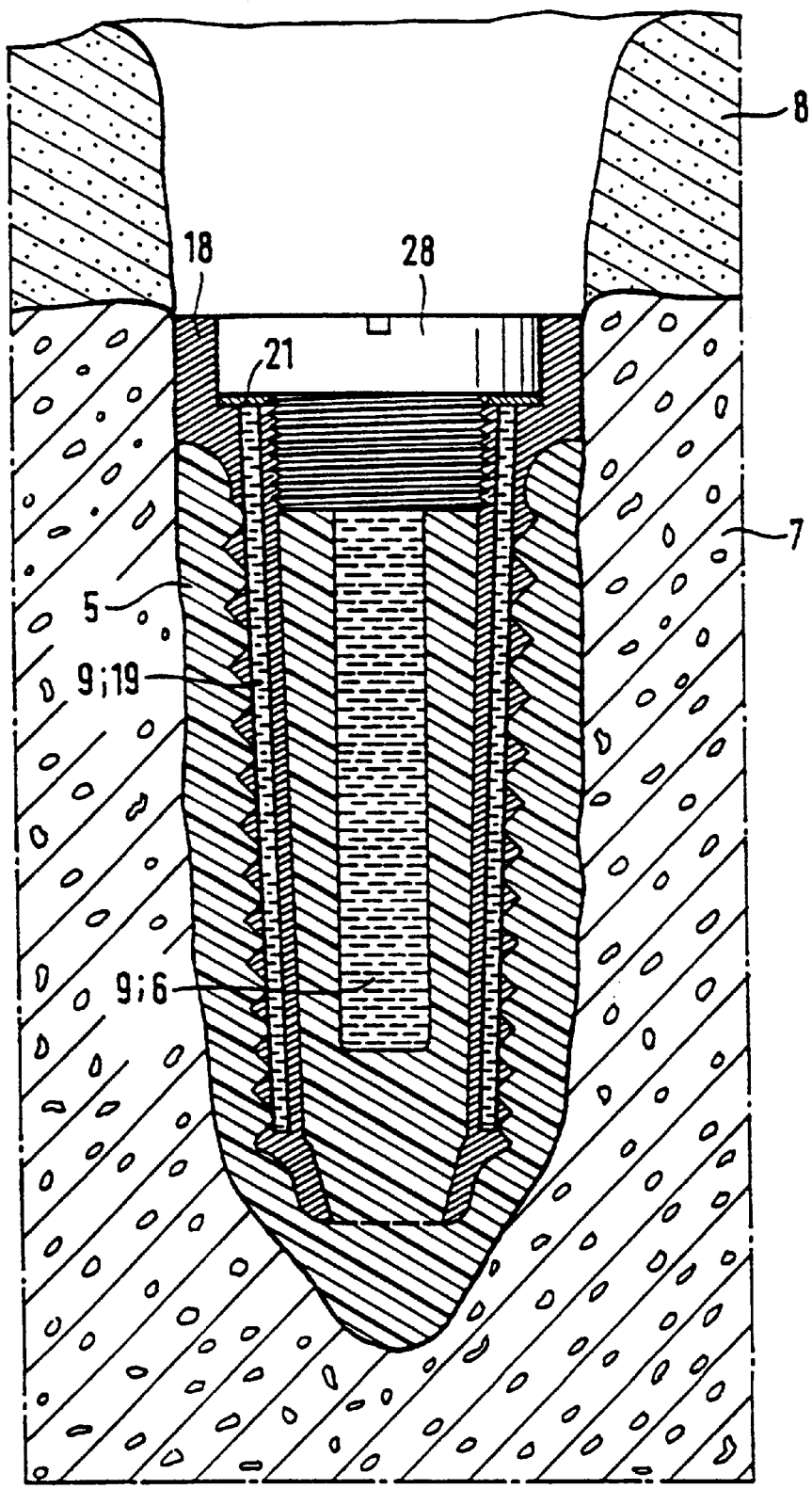
FIG. 18: Inserted implant with reservoirs closed by a screw cover

FIG. 18: FIG. 18 shows the implant 5 inserted into the jaw bone 7, whereby the gingiva is also shown. The packing ring 21, which closes off the inner spaces to outside influences such as bacteria, is positioned between the screw cover 28 and the hollow body 18.

The implant 5 fits exactly in the extraction socket, and the healing process can follow per primam through the close contact to the surrounding bones. The biodegradable material begins to reabsorb. When the reservoirs are opened due to the biodegradation process, the result is the release of the growth factors and/or active substances. This leads to the accelerated, controlled new formation of bone and a qualitatively optimized osseo-integration of the alloplastic implant core.

EXAMPLE 4

Another design is described below with reference to FIGS. 19–24.

Figure 19:
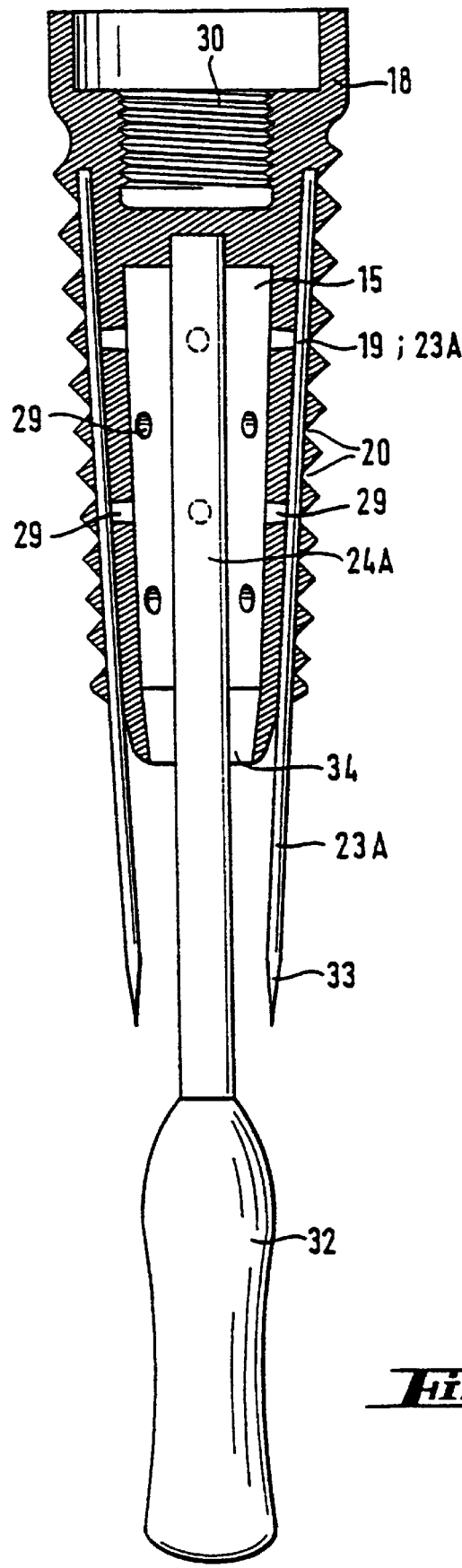
FIG. 19: Another working example of an implant core

FIG. 19: The hollow body 18, which consists of an osseo-integratable material, has an inner space 15 in the middle. Along the structured outer wall run elongated hollow spaces 19 corresponding to the working example described above. The hollow spaces 19 cross the grooves of the structured outer wall so that perforations 20 are formed that create a connection between the hollow spaces 19 and the outer surfaces of the hollow body 18. On the inner wall of the inner space 15 additional openings or perforations 29 to the outer surfaces are designed, whereby such openings 29 also exist in other working examples. The hollow body 18, which later serves as a fixture, has a screw thread 30 at the top, into which a temporary screw cover 31 can be screwed, whereby the screw thread 30 later serves as a means of affixing the tooth construction.

A rod-shaped mandrel 24 A with a handhold that ends in a handle 32, is stuck in the inner space 15 from below. Filament-shaped mandrels 23 A, which have a tip 33 at the lower end, are stuck in the hollow spaces 19 running along the outer wall.

Figure 20:
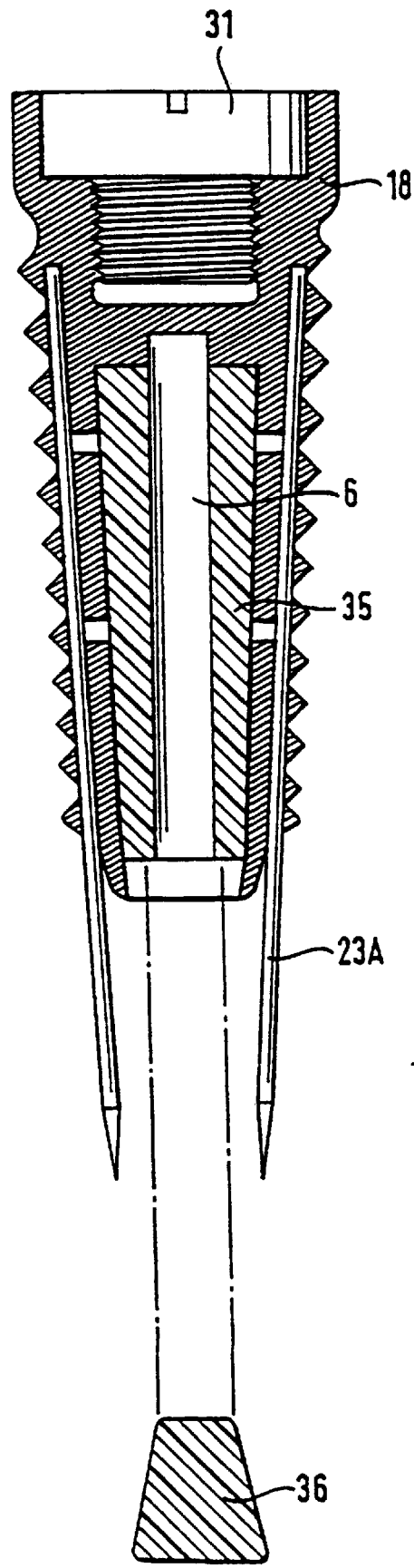
FIG. 20: Implant core according to FIG. 9 with an inner space partially filled with biodegradable material

FIG. 20: As a first step, biodegradable material is injected from the lower opening 34 and through the openings 29 into the annulus between the mandrel 24 A and the inner wall of the hollow body 18. After the material hardens, the mandrel 24 A is pulled out so that a layer 35 of the biodegradable material exists in the inner space 15.

FIG. 21: A first amount of the active substances 9 mentioned is poured into the hollow space 6, and the hollow space 6 is closed with a peg-shaped seal 36. The seal 36 also consists of the biodegradable material.

FIG. 22: The impression of the root of the tooth to be replaced is produced in the moulding material 1 by the known method—i.e., the cast cavity 2 is formed. The biodegradable material is poured into the cast cavity 2 and then the implant core is inserted into the cast cavity 2 in accordance with FIG. 21, whereby the tips 33 of the filament-shaped mandrels 23 penetrate the moulding material 1.

Figure 23:
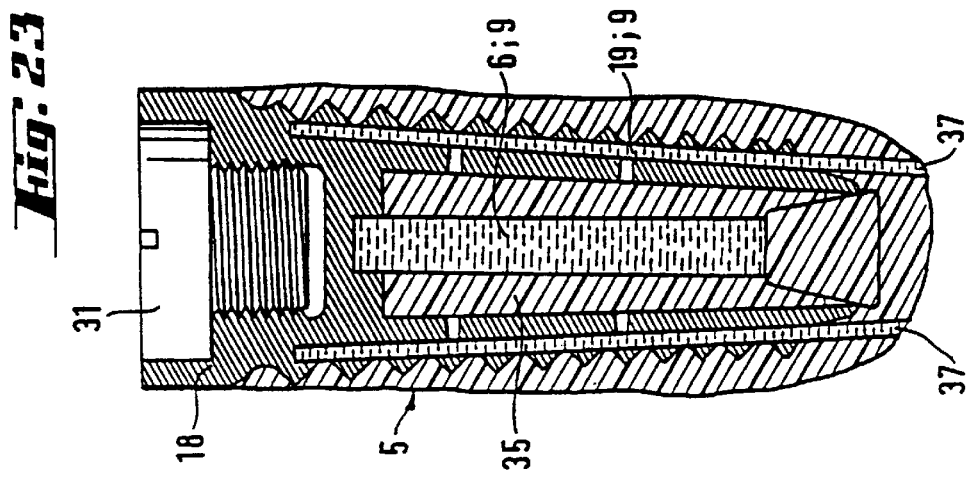
FIG. 23: Finished implant

FIG. 23: After the poured, biodegradable material thickens and hardens, the formed implant 5 is removed from the cast cavity 2 and the filament-shaped mandrels 23 A are pulled out of the implant core from below and the respective medical substances poured into the available spaces 19. The lower openings 37 of the filled spaces 19 are then closed. For this purpose, warmth caused by friction can be produced by using a rotating dental instrument, e.g., a rose-head burr, in the areas of the openings 37 so the biodegradable material melts at these sites and the openings 37 are closed.

Figure 24:
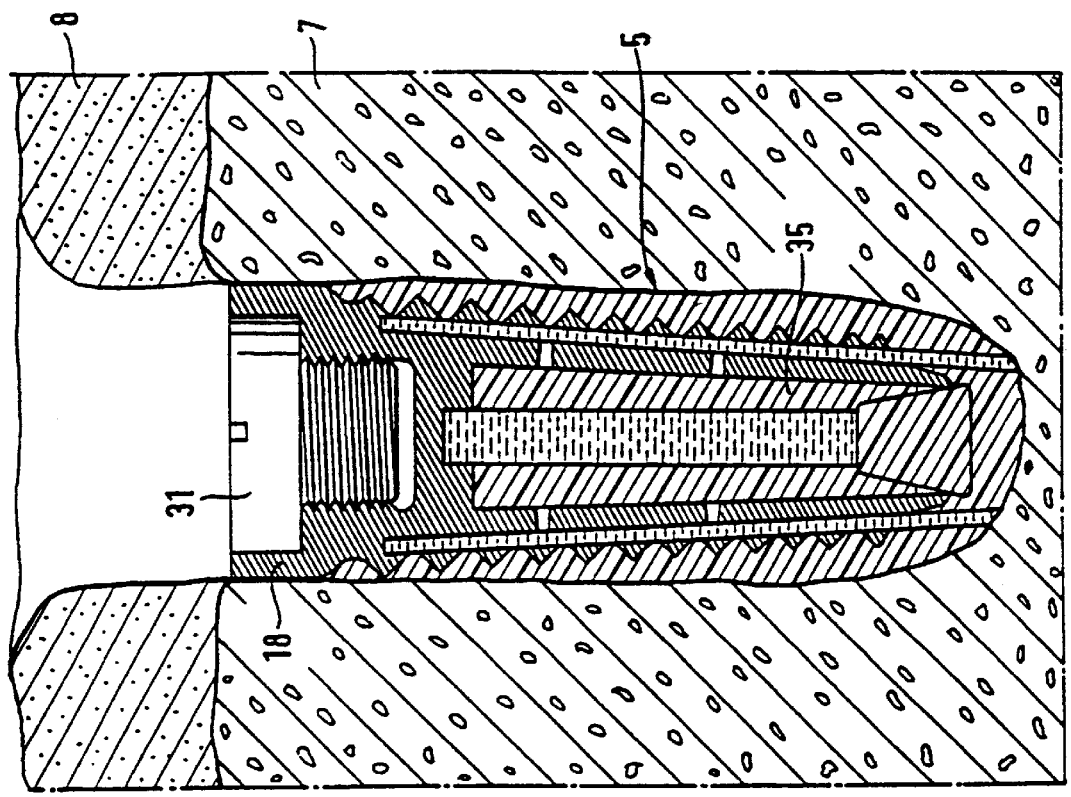
FIG. 24: Implanted implant

FIG. 24: The finished implant 5 can then be implanted in the extraction socket in accordance with the diagram in FIG. 24.

EXAMPLE 5

Figure 25:
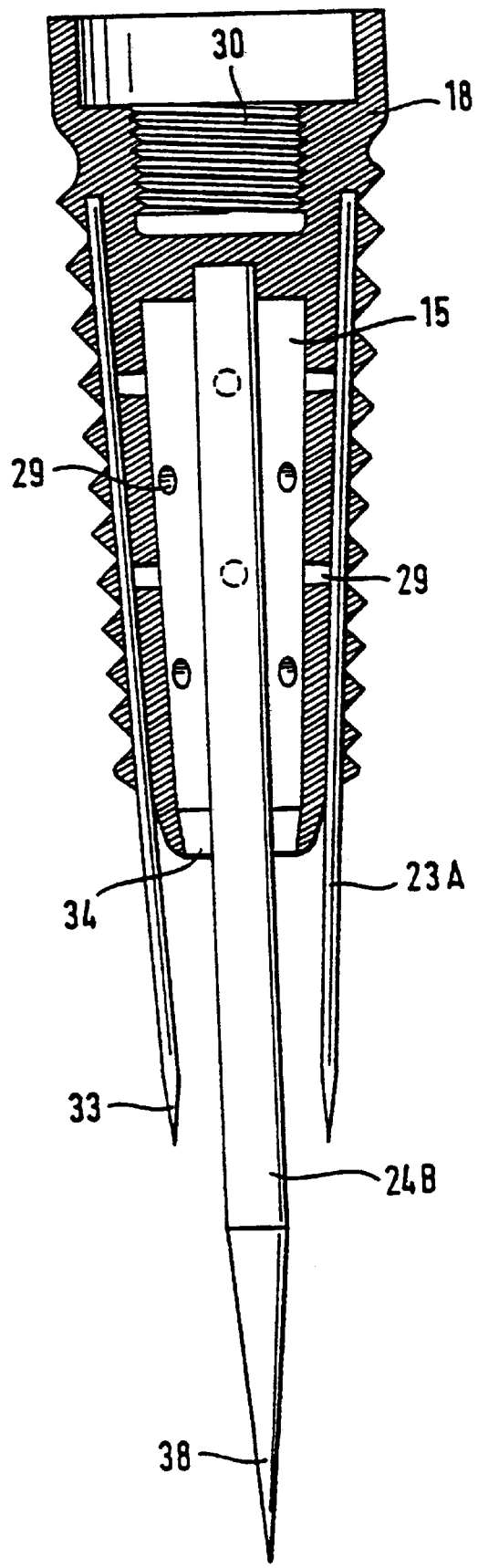
FIG. 25: Another working example of an implant core with mandrels
Figure 26:
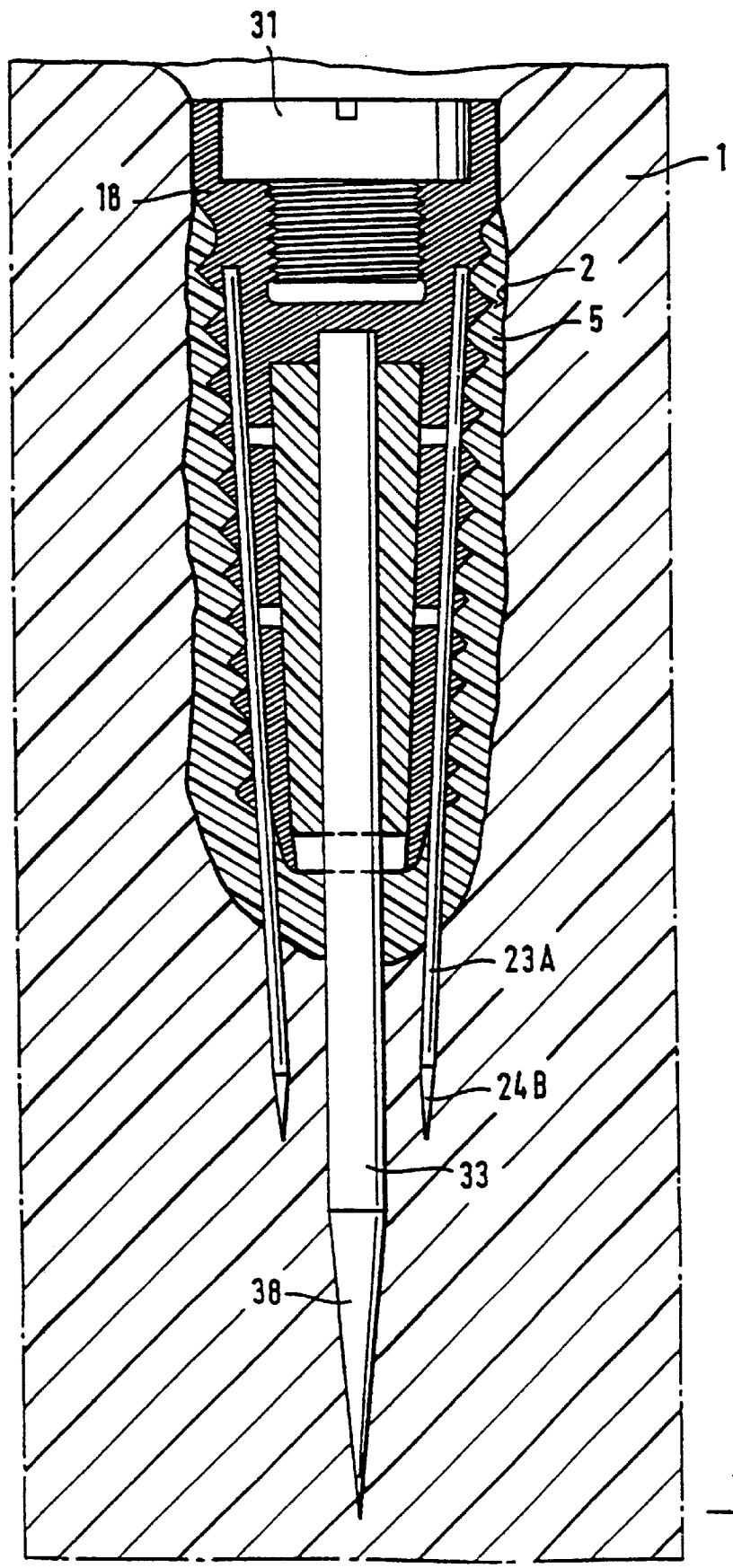
FIG. 26: Implant core according to FIG. 25 inserted into moulding material
Figure 27:
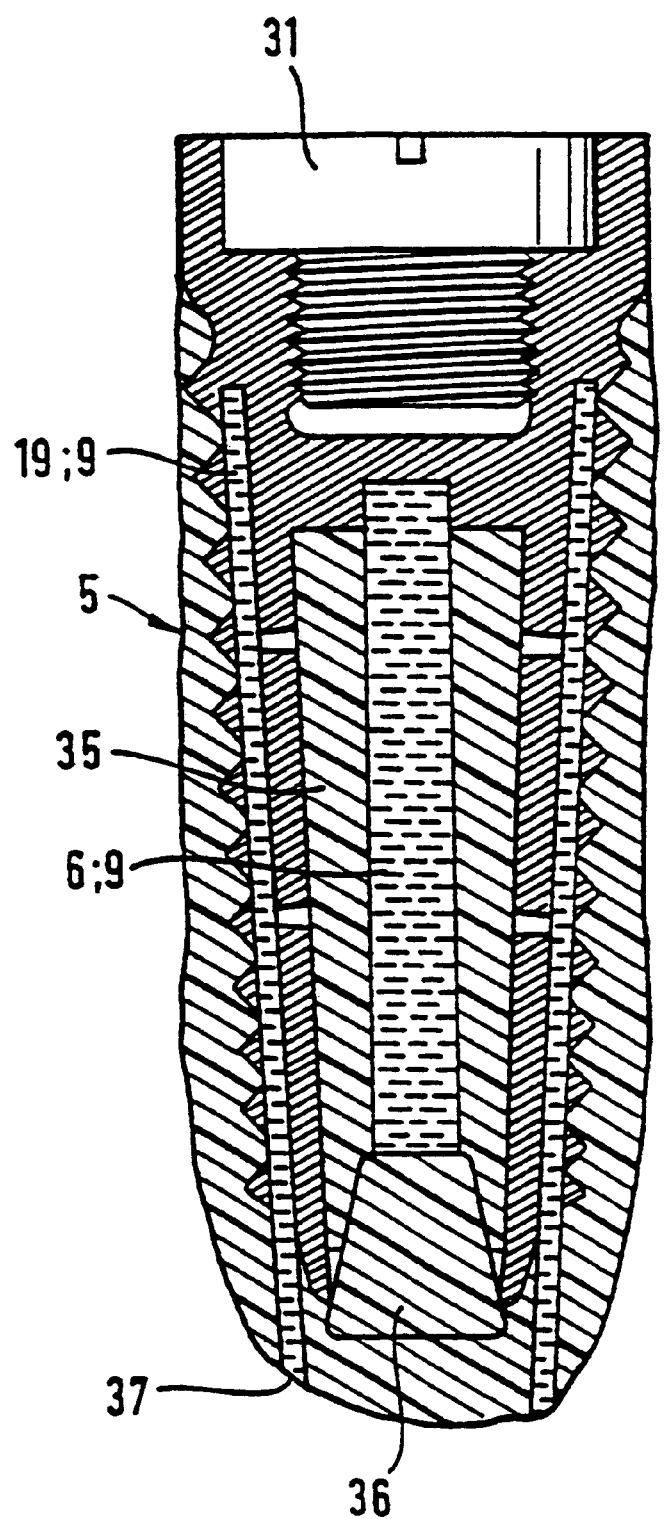
FIG. 27: Implant with an implant core in accordance with FIG. 25.

With the use of FIGS. 25–27 another working example is described. The steps in the procedure are analogous to those already described. Thus the process will be described below in simplified form.

FIG. 25: The hollow body 18 or implant core is analogous to the working example in accordance with FIG. 19. The rod-shaped mandrel 24, however, does not end in a handle; it ends in a tip 38.

FIG. 26: After the cast cavity 2 in the moulding material 1 is filled with the biodegradable material, the hollow body 18 is inserted into the cast cavity 2, whereby all of the tips 33, 38 of the mandrels 23, 24 are stuck into the moulding material. After the biodegradable material thickens and hardens, the mandrels 23, 24 are pulled out of the implant 5 from below and the existing spaces—the reservoirs—are filled with the corresponding medical substances. Then the inner space 15 is closed by the peg-shaped seal 36 and the spaces 19 running along the outer side of the implant core by the lower openings 37 are welded together by frictional heat so that the implant is obtained in accordance with FIG. 27.

FIG. 27: Finished implant with an implant core in accordance with FIG. 25.

In another variation that is not shown in the diagrams, one places a mandrel in the cast cavity 2, which runs vertically from the upper surface to the lowest point in the cast cavity 2. The mandrel is placed in the moulding material 1 in such a way that—after pouring the plastic materials in the cast cavity (2), letting it harden, and removing the formed implant and mandrel from the moulding material—one uses a pin provided with a screw thread (fixing pin or screw) made of a biocompatible, but not osseo-integratable, material—e.g. high-quality steel—instead of the mandrel. Its diameter at the shaft is smaller than the diameter of the mandrel. In this way a gap is formed that one can fill with bioactive substances. In another design, the shaft of the pin provided with a screw thread can be longer than the mandrel and its screw thread can cut the lowest point of the cast cavity (2). The fixing screw, extended in this way and cutting its own screw thread, is screwed into the jaw bone through the deepest point of the extraction socket.

If during the healing phase the biodegradable material is replaced by bone material under the effect of the biologically active material, the fixing screw is surrounded by bone material on all sides. Because the screw is not osseo-integratable, it can be removed easily. The channel that remains in the jaw bone makes possible the insertion of an exactly matched fixture in its natural direction with respect to the axis. As an alternative to this, one can leave a suitably formed osseo-integratable fixing screw in the jaw bone and provide it with an implant suprastructure to use as a fixture.

The advantage of this variation is that an extraction and implantation can be carried out with one therapeutic treatment. Through the presence of biologically active substances on the surface of the implant an especially effective wound closure of the bordering tissue takes place, as well as the quick osseo-integration of the implant fixture.

EXAMPLE 6

The object of variation (b) of the invention is described in greater detail below.

The cast cavity 2, e.g., an extraction socket, is reproduced in the above-mentioned drawings. As an alternative to the design pictured with the mandrels, one can use the extraction sockets or the extraction sockets shown in the moulding material of a porous matrix made of synthetic polymers or a natural material that contains biologically active substances and fill the hollow spaces of this matrix with the hardening plastic material. Suitable synthetic polymer materials are, preferably, macrostructured and can be sponge-shaped forms with a perforated skeleton framework made of a polymer material, in which gaps connecting under each other and pores are dispersed. Suitable materials are, for instance, polycarbonates, polyorthoesters, PGA, PLA, or mixtures of them, etc. Such a design is especially suitable for a dispensing unit that holds the biologically active substance to be dispensed in its polymer structure until it is dispensed.

A porous matrix made of natural material is, preferably, a dentin matrix, which can be obtained by extracting teeth or tooth fragments.

EXAMPLE 7

The production of a dentin matrix from material suitable for a patient is described by way of example. One removes the cement and pulp mechanically according to the procedure described by K. Bessho, et al., in the *Journal of Dental Research* 70 (1991), pp. 171–75. The tooth matter up to the size of a particle of approximately 1 mm$^3$ is ground in a grinder. The ground material is washed in warm water, the oils removed by immersing it in a (1:1) chloroform/methanol solution for 12 hours, and the material is demineralized with a 0.5 molar HCl solution for 72 hours at 4° C. Oils are again removed from the demineralized material 12 hours long by immersing it in a (1:1) chloroform/methanol solution for 6 hours, and then the material is treated for 24 hours in a 2-molar calcium-chloride solution, for four hours in a 0.5 molar EDTA solution at 7.4 pH, and for 24 hours in an 8-molar lithium-chloride solution, and then washed in distilled water at 4° C. One extracts the material pretreated in this way for 96 hours at 4° C. with a 20-fold volume of a 4-molar guanidine-HCl solution. One centrifuges the extract (10,000 g. 30 min. at 4° C.) and concentrates (1:5) the filtrate through ultrafiltration (Diaflo®-membrane YM-10; 10,000 mole weight fraction, Amicon Ireland). One adds to the concentrate three portions of ethanol cooled to −20°. The mixture is allowed to stand for 12 hours at 4° C. and centrifuged (10,000 g. 30 min. at 4° C.); and a concentrate that contains ethanol and an ethanolic residue is obtained. One washes the residue with distilled water and dialyzes it with a 10-fold volume at 4° C. for 72 hours until the formation of the precipitate is completed, whereby the distilled water is changed every 12 hours. One centrifuges the dialyzed residue (70,000 g. 30 min. at 4° C.) for the purpose of dividing it into water-soluble and water-insoluble fractions, lyophilizes it, and determines the weight.

In the moulding material the reproduced cast cavity of an extraction socket is filled with a mixture made of PGA/PLA copolymers and the matrix material that is made of dentin and contains BMP; and a root implant with fixture, which one inserts into the jaw bone at the intended site, is formed in the way already described above.

The invention is described herein by the written description, drawings, examples and the claims appended hereto. Variations and modifications of the invention will be apparent to one of ordinary skill in the art based on a reading of these teachings. These variations and modifications are intended to be encompassed by the claims.

International patent application PCT/EP96/05506, filed Dec. 10, 1996 and Swiss patent application 3565/95, filed Dec. 18, 1995 are relied upon and incorporated herein by reference.

What is claimed is:

1. A medical implant (5) for inserting into a space with a pre-specified dimension and for filling a cast cavity (2) with a hardening plastic material with mineral components on the basis of calcium and phosphate or, in the case of the new formation of bone, a biodegradable material, or a combination of both, which is obtained by:
   a) placing at least one mandrel (3; 23, 24) in the cast cavity (2) in such a way that it can be removed from the cast cavity (2) of the formed implant (5) after the plastic material hardens and creating, with the removal of the mandrel, a space (6; 19) that extends from the inner area of the implant (5) to the outer surface, thus forming a reservoir that can be filled with a biologically active substance, or
   b) filling the case cavity (2) with a porous matrix and a biologically active substance, and the hollow spaces of this matrix with the hardening plastic material.

2. A medical implant (5) according to claim 1, which is obtained by forming the cast cavity (2) as an impression of an extracted tooth.

3. A medical implant according to claim 1, which is obtained by using mandrels designed as filament-shaped or rod-shaped mandrels (3) and forming the reservoirs as channel-shaped or capillary-shaped spaces.

4. A medical implant according to claim 1, which is obtained by using, for the biodegradable material, an osteo-conductive polymer.

5. A medical implant according to claim 1, which is obtained by filling, as a biologically active substance, an active ingredient with osteo-inductive properties.

6. A medical implant according to claim 1, which is obtained by filling the reservoir with a biologically active substance, a protein with the properties of a transforming growth factor of the type beta (TGF-β) or combinations of them.

7. A process for the production of a medical implant (5), which comprises forming a cast cavity (2) in molding material (1) in the form of an impression of an extracted tooth or resected bone;
- filling this cast cavity (2) with a hardening material with mineral components on the basis of calcium or phosphate, or a biodegradable material;
- placing at least one mandrel (3; 23; 24) in the cast cavity in such a way that it can be removed from the cast cavity of the formed implant (5) after the plastic material hardens; creating with the removal of the mandrel a space (6; 19) that serves as a reservoir and extends from the inner area of the implant (5) to the outer surface;
- removing the formed implant (5) from the cast cavity and, after removing the mandrels (3; 23; 24), filling the reservoir with a biologically active substance.

8. A process according to claim 7, which comprises inserting an alloplastic, osseo-integratable fixture in the cast cavity (2).

9. A process according to claim 7, which comprises first inserting into the cast cavity (2) several mandrels (3; 23, 24), which run from the cast cavity (2) to the molding material (1) and are arranged in such a way that one removes the mandrels (3; 23, 24) from the implant after filling the cast cavity (2) with the plastic molding material, letting it harden, and removing the formed implants (5) from the cast cavity (2).

10. A process according to claim 7, which comprises producing a medical implant as a dispensing unit for biologically active substances.

* * * * *